United States Patent [19]

Marcoux

[11] Patent Number: 4,696,924
[45] Date of Patent: Sep. 29, 1987

[54] METHOD FOR USING DILTIAZEM FOR TREATING STROKE

[75] Inventor: Frank W. Marcoux, Ann Arbor, Mich.

[73] Assignee: Warner-Lambert Company, Morris Plains, N.J.

[21] Appl. No.: 893,841

[22] Filed: Aug. 6, 1986

Related U.S. Application Data

[62] Division of Ser. No. 818,505, Jan. 10, 1986, Pat. No. 4,654,372.

[51] Int. Cl.⁴ ............................................. A61K 31/55
[52] U.S. Cl. .................................................. 514/211
[58] Field of Search ......................................... 514/211

[56] References Cited

PUBLICATIONS

Chem. Abst. 98-212475g, (1983).
Chem. Abst. 104-14791m, (1986), referring to article J. Neurosurg., (1985), 63(6), 929-36.

Primary Examiner—Stanley J. Friedman
Attorney, Agent, or Firm—Joan Thierstein

[57] ABSTRACT

The present invention is a method of use for the treatment of stroke with one of diltiazem, verapamil, or nifedipine.

1 Claim, No Drawings

METHOD FOR USING DILTIAZEM FOR TREATING STROKE

This is a division of application Ser. No. 818,505, filed Jan. 10, 1986, now U.S. Pat. No. 4,654,372.

BACKGROUND OF THE INVENTION

It is suggested in the literature, that pharmacologic agents are currently under study for cerebral resuscitation and such agents include calcium antagonists. See generally, N. G. Bircher, "Ischemic Brain Protection," Ann. Emerg. Med., 14:8 August 1985, pp 784-788 and S. E. Gisiold and P. A. Steen, "Drug Therapy in Brain Ischaemia", Br. J. Anaesth., 57, (1985), pp 96-109.

After a general disclosure of the value of calcium entry blockers in circulatory disorders results of selected clinical studies with flunarizine by A. Kappert, in "The Clinical Value of Calcium Entry Blockers in Circulatory Disorders. Effect of Flunarizine in Cerebro-Vascular and Peripheral Vascular Diseases," Inter. Angio., 3, 1984, pp 43-50, are said to show a positive, well documented effect on the symptoms of cerebrovascular insufficiency and on intermittent claudication in peripheral arteriosclerosis. Specific indications suggested by A. Kappert as a result of his clinical studies are migraine and vertigo. The mechanism of such effect and any significance for other calcium antagonists from these studies is not known and not predictive for the utility of the present invention, i.e., the treatment of occlusive stroke. In fact, flunarizine is not active in the assay described hereinafter as the combined middle cerebral and ipsilateral common carotid artery occlusion (MCAO) in the rat. This is essentially a well-recognized screen for compounds active against stroke now used to show the method of use for compounds having activity for the treatment of stroke of the present invention. Thus, although it is reported by J. K. Deshpande and T. Wielock in the article "Amelioration of Ischemic Brain Damage by Postischemic Treatment with Flunarizine, Neurological Research, 1985, Volume 7, March, pp 27-29, that flunarizine significantly reduced neuronal necrosis, the same authors readily admit that the etiologic processes involved in the damage that follows an ischemic insult still have not been clearly defined.

In fact, D. P. Reedy, et al, "Effects of Verapamil on Acute Focal Cerebral Ischemia," in Neurosurgery, Vol. 12, No. 3, 1983, pp 272-6, report that verapamil, that is also a Ca++ entry blocking agent, did not improve regional cerebral blood flow and did not protect ischemic brain in acute focal cerebral ischemia. J. R. Berger, et al, "Calcium Channel Blocker: Trial in Global Brain Ischemia," Neurology, p 183, 33[Suppl. 2] April 1983 also studied the efficacy of verapamil in preventing ischemic brain injury in rats concluding that the results of this study suggest that calcium channel blockers are ineffective in the treatment of severe brain ischemia.

The unpredictability of a calcium blocker generally and specifically, i.e., nimodipine, is apparent in discussions by A. I. Faden, et al, "Evaluation of the Calcium Channel Antagonist Nimodipine in Experimental Spinal Chord Ischemia," J. Neurosurg., Vol. 60, April, 1984, pp 796-9 and P. A. Steen, et al, "Nimodipine Improves Cerebral Blood Flow and Neurologic Recovery After Complete Cerebral Ischemia in the Dog, Journal of Cerebral Blood Flow and Metabolism, 3:38-43, 1983.

Finally, although nine drugs; D-600, diltiazem, flunarizine, nicardipine, nifedipine, nimodipine, nitrendipine, verapamil, and triapamil, were studied against induced hypoxia and hyperexcitability by A. Wauquier, et al, "Calcium Entry Blockers as Cerebral Protecting Agents: Comparative Activity in Tests of Hypoxia and Hyperexcitability," Japan J. Pharmacol., 38, pp 1-7 (1985), the studies are not specifically indicative of activity of a method of use for the treatment of stroke as now found in the present invention.

Selected compounds which inhibit calcium influx in cells of vascular tissue are generally known antiischemic agents. For example, see European Patent Application No. 0 132 375 showing utility for antiischemic agents as useful in the treatment or prevention of a variety of cardiac conditions. Thus, although A. Wauquier, et al, says his tests are for brain hypoxia, the tests show effects on decapitated male rats and as such do not teach the present method of treating stroke. Similarly, the antiischemic effects of A. Wauquier, et al, are shown by general studies of the kind supporting the usefulness disclosed in European Patent Application No. 0 132 375 discussed immediately above. Thus, no teaching in A. Wauquier, et al, shows treatment of stroke.

For the above reasons, the present invention relates to the now discovered novel method of use for the treatment of stroke with a compound known as diltiazem, verapamil, or nifedipine in an effective amount for treating stroke in unit dosage form.

SUMMARY OF THE INVENTION

Accordingly, the present invention also reates to a method of use for treating stroke, preferably occlusive stroke, in a subject suffering therefrom, comprising administering to said subject a compound selected from the group consisting of diltiazem, verapamil, or nifedipine, in an effective amount for treating stroke. The compound may be administered in admixture with a pharmaceutically acceptable carrier in a unit dosage form.

Diltiazem is also known as 3-(acetyloxy)-5-[2-dimethylamino)-ethyl]-2,3-dihydro-2-(4-methoxy-phenyl)-1,5-benzothiazepin-4(5H)-one; or (+)-cis-5-[2-dimethylamino]ethyl]-2,3-dihydro-3-hydroxy-2-(p-methoxyphenyl)-1,5-benzothiazepin-4(5H)-one acetate(ester). This invention is also understood to include the hydrochloride salt thereof.

Verapamil is also known as α-[3-[[2-(3,4-dimethoxyphenyl)ethyl]methylamino]propyl]-3,4-dimethoxy-α-(1methylethyl)benzeneacetonitrile; 5-[(3,4-dimethoxyphenethyl)methylamino]-2-(3,4-dimethoxyphenyl)-2-isopropylvaleronitrile; α-isopropyl-α-[(N-methyl-N-homoveratryl)-γ-amino-propyl]-3,4-dimethoxyphenylacetonitrile; or iproveratril. It is understood the hydrochloride salt of this compound is also the invention.

Nifedipine is also known as 1,4-dihydro-2,6-dimethyl-4-(2-nitrophenyl)-3,5-pyridinedicarboxylic acid dimethyl ester; or 4-(2'-nitrophenyl)-2,6-dimethyl-3,5-dicarbomethoxy-1,4-dihydropyridine.

Diltiazem may be prepared by a method disclosed in U.S. Pat. No. 3,562,257 which is incorporated herein by reference.

Verapamil may be prepared by a method disclosed in U.S. Pat. No. 3,261,859 which is incorporated herein by reference.

Finally, nifedipine may be prepared by a method disclosed in U.S. Pat. No. 3,485,847 which is incorporated herein by reference.

Each of diltiazem, verapamil, and nifedipine are also available commercially.

DETAILED DESCRIPTION

The compounds noted for the method of treatment stroke of the present invention are known as cardiac drugs with calcium blocking activity. Specifically each compound is known to provide one of the accompanying advantageous effects. The effects include benefits for coronary arterial spasm, for decreasing peripheral vascular resistance resulting in a modest fall in blood pressure, and in exercise tolerance studies in patients with ischemic heart disease, and also the effects reduce the heart rate-blood pressure product for a given work load, antifibrillation, and antianginal effect. Such effects, increase myocardial oxygen delivery and at the same time reduces myocardial energy consumption and oxygen requirements. In other words, the compounds for use in the present invention have heretofore not been recognized for CNS use.

The present invention, however, relates to the discovery that the compounds named above have activity for a novel method of use specifically for treating strokes. The stroke as referred to in the present invention is a cerebrovascular disease and may also be referred to as cerebrovascular accident (CVA) and specifically includes acute stroke. Also included in cerebrovascular disease are transient cerebral ischemic attacks and other cerebrovascular problems accompanied by cerebral ischemia. An ordinarily skilled physician would be able to determine the appropriate diagnosis of stroke for administration of this intention.

According to this invention, a compound selected from the group ditiazem, verapamil, and nifedipine, which is an agent for treating stroke herein, is administered in an effective amount which comprises a total oral daily dosage of diltiazem or of verapamil of about 30 to 500 mg, preferably 240 to 480 mg and of nifedipine of about 1 to 80 mg, preferably 40 to 75 mg to a human suffering from stroke. Such daily dosages specifically for an adult human can be used in a single administration of the total amount or in divided doses. Generally, a large initial dose is followed by a series of lesser doses to maintain plasma blood levels, daily is preferred. Thus, the preferred dosage is about 10 to 20 mg four times of nifedipine daily, or about 30 to 80 mg of diltiazem or verapamil four to six times daily.

The preferred route of administration is that deemed preferred as judged by the physician. For example, in acute stroke, intravenous administration may be preferred. On the other hand in high risk stroke patients oral administration may be preferred. Variations within these dosages may depend on the age, size, or individual characteristics of the subject being treated. In particular subjects it may be preferrable to begin dosages at a level acceptable from the presently known cardiovascular utility and to monitor side-effects, using amounts to the desired dosage for treating stroke.

The pharmaceutical compositions for the method of use can take any number of a wide variety of oral and parenteral dosage forms. The dosage forms comprise as the active component, one of diltiazem, verapamil, or nifedipine as defined above. Such pharmaceutical compositions are from among those of the ordinary skill in the art. Particularly, the compositions of each of diltiazem, verapamil, and nifedipine which are commercially available are compositions for use in the method of use in the present invention.

For preparing pharmaceutical compositions, one uses inert, pharmaceutically acceptable carriers that can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders, or tablet disintegrating agents; it can also be an encapsulating material. In powders, the carrier is a finely divided solid which is in admixture with the finely divided active compounds. In the tablet, the active compounds are mixed with carrier having the necessary binding properties in suitable proportions and compacted in the shape and size desired. The powders and tablets preferably contain from 5% or 10% to about 70% of active ingredients. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, cocoa butter, and the like. The term "preparation" is intended to include the formulation of the active compounds with encapsulating materials as carrier, providing a capsule in which the active components (with or without other carriers) are surrounded by carrier, which are thus in associate with it. Similarly, cachets are included. Tablets, powders, cachets, and capsules can be used as solid dosage forms suitable for oral administration.

Liquid form preparations include solutions, suspensions, and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspensions suitable for oral use can be made by dispersing the finely divided active components in water with viscous material, i.e., natural or synthetic gums, resins, methyl cellulose, sodium carboxymethyl cellulose, and other well-known suspending agents.

Preferably, the pharmaceutical preparation is in unit dosage form. In such form, the preparation is subdivided into unit doses containing appropriate quantities of active components. The unit dosage form can be packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The quantity of active compounds in a unit dose of preparation may be varied or adjusted from 1 mg to 200 mg according to the particular application and the potency of the active ingredients as indicated by the daily dosage noted above.

In therapeutic use as an agent for treating stroke, the compositions are constituted such that the active ingredients content can be conveniently at the initial oral dosage for nifedipine of about 0.10 to 0.20 mg per kilogram and for diltazem or verapamil of about about 0.40 to 1.75 mg per kilogram of weight. An active ingredients content such as to give a dose range for nifedipine of about 0.14 mg and for diltiazem or verapamil of about 0.85 mg of active ingredients per kilogram is preferred.

The pharmaceutical compositions preferably are constituted so that they can be administered parenterally or orally. Solutions of the active compounds as free bases and free acids or pharmaceutically acceptable salts can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, paragens, chlorobutanol, phenol, sorbic acid, thimerosal, and the like. In many cases, it will be preferable to include isotonic agents, for example, sugars or sodium chloride. Prolonged absorption of the injectable compositions of agents delaying absorption, may be accomplished with, for example, aluminum monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients, into a sterile vehicle which contains the basic dispersion medium and the required other ingredients from those enumerated above. In the case of the sterile powders for the preparation of sterile injectable solutions, the preferred methods of preparation are vacuum drying and the freeze-drying technique which yield a powder of active ingredients plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well-known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral or intravenous compositions in dosage unit form for ease of administration and uniformity of dosage. Dosage unit form as used herein refers to physically discrete units suitable as unitary dosages for the mammalian subjects to be treated; each unit containing a predetermined quantity of active materials calculated to produce the desired therapeutic effect in association with the required pharmaceutical carrier. The specification for the novel dosage unit forms of the invention are dictated by and directly dependent on (a) the unique characteristics of the active materials and the particular therapeutic effect to be achieved, and (b) the limitation inherent in the art of compounding such active materials for the treatment of disease in living subjects having a diseased condition in which bodily health is impaired as herein disclosed in detail.

The principal active ingredients are compounded for convenient and effective administration in effective amounts with a suitable pharmaceutically acceptable carrier in dosage unit form as hereinbefore disclosed. A unit parenteral dosage form can, for example, contain the principal active compounds in amounts of diltiazem or verapamil ranging from about 2.5 to about 10 mg, with from about 5 to 10 mg being preferred and in amounts of nifedipine ranging from 0.025 to about 0.10 mg with 0.05 to 0.1 mg being preferred. Expressed in proportions, the active compounds of diltiazem or verapamil are generally present in from about 0.5 to about 2.5 mg/ml of carrier and of nifedipine is generally present in from about 0.005 to about 0.025 mg/ml of carrier. The daily parenteral doses for humans to be treated with diltiazem or verapamil ranges from 0.075 to 0.225 mg/kg. The preferred daily dosage range is 0.075 to 0.15 mg/kg. Parenteral doses of nifedipine ranges from 0.008 to 0.0023 mg/kg daily.

The usefulness of the active compounds, diltiazem, verapamil, or nifedipine, in a method of use for treating stroke of the present invention is demonstrated by administration of the active compounds in an essentially standard pharmacological test procedure as described and illustrated in the following assay.

ASSAY

Combined Middle Cerebral and Ipsilateral Common Carotid Occlusion in the Rat as a Screen for Compounds Active in the Treatment of Stroke (MCAO)

Occlusion of the proximal part of the middle cerebral artery (MCA) is a common cause of stroke in man and can be accomplished surgically in experimental animals. This technique, though technically feasible in the rat (A. Tamura, et al, Focal Cerebral Ischemia in the Rat: 1. Description of Technique and Early Neuropathological Consequences Following Middle Cerebral Artery Occlusion. *J. Cereb. Blood Flow Metab.* 1:53–60, 1981), is very difficult and time-consuming. It has been reported that a distal occlusion of the MCA 5 mm from its origin at the circle of Willis does not consistently result in infarction (P. Coyle, Middle Cerebral Artery Occlusion in the Young Rat. *Stroke* 13:6, 1982). In the present assay distal MCA occlusion is combined with ipsilateral common carotid ligation in an attempt to produce reproducible, focal cerebral ischemic infarcts.

Adut male Fisher (F-344) rats (250–300 g) are anesthetized in a box containing halothane and then moved to a small animal anesthetic mask (D. E. Levy, et al, A Mask for Delivery of Inhalation Gases to Small Laboratory Animals. *Laboratory Animal Science,* Volume 30, 5:868–870, 1980) to which 1.5% halothane in room air is provided for spontaneous inspiration. The skin on the ventral side of the neck and the left temporal-parietal region is shaved. An incision is made in the neck and the left common carotid artery is doubly ligated and cut between the sutures. The incision is infiltrated with local anesthetic and closed with 4-0 silk. Another incision is then made behind the left eye and the skin is held back with retracters. The exposed temporalis muscle is electrocauterized (Jarit Bipolar Coagulator) and partially removed. The upper part of the lower jaw bone is also removed. Deep surgery is performed with the aid of a Zeiss OPMl 99 surgical microscope. A 1 to 2-mm diameter craniotomy is made about 1 mm anterior to where the rostral end of the zygoma fuses to the squamosal bone. To prevent the drill from going through the dura, the burr hole is not drilled completely through the skull. Bone remaining after drilling is removed with forceps. The dura is pierced and reflected with a fine probe.

At this point the rat is injected with 0.3 ml of 2% Evans blue dye in saline via the tail vein. Evans blue binds to serum albumin and will not pass the blood-brain barrier unless damage has occurred, such as damage induced by ischemia. A small hook is then positioned under the MCA and the MCA is lifted away from the cortex. A 3eweler-type bipolar forceps is introduced and the MCA is electrocauterized and separated. Gelfoam ® is put over the craniotomy and wound is closed with 4-0 silk. The rats are then taken off the Jena Citoval ® microscope with a drawing tube and an Apple II plus computer with a Houston Instrument digitizing pad, we employed a software routine to measure the area of the ischemic damage as indicated by the extent of Evans blue tissue extravasation. The software package is purchased from R +M Biometrics (Nashville, TN) and is titled Bioquant II. From the lesion areas ($MM^2$) obtained from the Bioquant II program, we estimate the hemispheric extent ($mm^3$) of ischemic damage between the anterior and posterior sections by computing and adding the volume of two truncated cones.

In preliminary experiments the extent of cerebral ischemic injury was compared to MCAO and sham-operated rats. Sham-operated rats underwent an identical surgical procedure except that the biopolar electrocautery forceps were activated away from the artery but within the subarachnoid space.

The effects of MCA and ipsilateral common carotid artery occlusion on the areas of ischemic damage are summarized by coronal section in the following Table 1. The data for the hemispheric volume of ischemic damage are summarized in the following Table 2. Thus, a comparison of infarct size in the sham-operated versus MCAO rats is shown.

TABLE 1

The Effects of Middle Cerebral and Ipsilateral Common Carotid Artery Ligation on the Area of Ischemic Damage in the Rat

| Rat No. | Anterior Section | | | Middle Section 1 | | | Posterior Section | | |
|---|---|---|---|---|---|---|---|---|---|
| | Area of Coronal Section ($mm^2$) | Area of Infarction ($mm^2$) | Infarct as % of Coronal Section | Area of Coronal Section ($mm^2$) | Area of Infarction ($mm^2$) | Infarct as % of Coronal Section | Area of Coronal Section ($mm^2$) | Area of Infarction ($mm^2$) | Infarct as % of Coronal Section |
| Sham-Operated Rats | | | | | | | | | |
| 1 | 89.585 | 3.263 | 3.64 | 113.940 | .580 | 0.51 | 140.505 | 1.856 | 1.32 |
| 2 | 82.946 | 2.174 | 2.62 | 104.668 | .445 | 0.43 | 133.266 | .473 | 0.35 |
| 3 | 84.844 | 1.913 | 2.25 | 106.163 | 1.114 | 1.05 | 133.996 | .443 | 0.33 |
| 4 | 85.601 | 4.232 | 4.94 | 111.661 | 3.590 | 3.22 | 135.517 | 0 | 0 |
| 5 | 85.893 | 5.537 | 6.45 | 108.703 | .561 | 0.52 | 140.198 | 0 | 0 |
| Mean +/− SE | 85.77 ± 1.08 | 3.42 ± 0.67 | 3.98 ± 0.77 | 109.03 ± 1.71 | 1.26 ± 0.59 | 1.15 ± 0.53 | 136.70 ± 1.54 | 0.55 ± 0.34 | 0.40 ± 0.24 |
| MCAO Rats | | | | | | | | | |
| 1 | 80.424 | 15.646 | 19.45 | 104.474 | 15.282 | 14.63 | 129.618 | 17.485 | 13.49 |
| 2 | 77.808 | 6.255 | 8.04 | 107.250 | 14.110 | 13.16 | 131.076 | 4.641 | 3.54 |
| 3 | 84.094 | 11.224 | 13.35 | 109.135 | 11.785 | 10.80 | 135.916 | 3.179 | 2.34 |
| 4 | 81.608 | 8.385 | 10.27 | 107.617 | 8.260 | 7.68 | 125.504 | 0.797 | .64 |
| 5 | 75.317 | 6.540 | 8.68 | 100.766 | 12.860 | 12.76 | 133.632 | 13.659 | 10.22 |
| Mean +/− SE | 79.85 ± 1.52** | 9.61 ± 1.75** | 11.96 ± 2.09*** | 105.85 ± 1.48 | 12.46 ± 1.20**** | 11.81 ± 1.20**** | 131.5 ± 1.78* | 7.95 ± 3.23 | 6.05 ± 2.47 |

[1]The middle section was made at the level at which the MCA was ligated; The Anterior Section was 2 mm anterior and the Posterior section was 2 mm posterior to the Middle Section.
Comparisons by coronal section were made between Sham-Operated and MCAO Rats using a non-paired Students T-test. * = $p < .05$,  = $p < .02$, * = $p < .01$, **** = $p, .001$.

halothane and allowed to wake up. Total anesthesia time is typically 30 minutes. Animals undergoing this procedure (MCAO rats) awake from anesthesia within ten minutes of breathing room air alone again and are grossly indistinguishable from unoperated rats.

On Day 2 following MCA occlusion, the rats were anesthetized with ketamine (150 mg/kg, IP) and sacrificed. Cerebral tissue fixation is initiated by perfusion of 10% neutralized, buffered formalin for five minutes. Brains are removed and stored in the fixitive until analysis.

For evaluation of the extent of cerebral ischemic injury the brains were cut coronally in three different locations. The first section is at the level where the MCA was ligated. The other two sections are 2 mm anterior and 2 mm posterior to the first. Using an aus-

TABLE 2

The Effects of Middle Cerebral and Ipsilateral Common Carotid Artery Ligation on Hemispheric Ischemic Damage in the Rat

| Rat # | Sham Operated Rats Hemispheric Ischemic Damage ($mm^3$) | MCAO Rats Hemispheric Ischemic Damage ($mm^3$)[1] |
|---|---|---|
| 1 | 5.80 | 63.67 |
| 2 | 3.32 | 37.74 |
| 3 | 4.50 | 37.07 |
| 4 | 10.20 | 24.40 |
| 5 | 5.61 | 45.57 |
| *Mean ± SE | 5.89 ± 1.17 | 41.69 ± 6.46 |

[1]Hemispheric ischemic damage was estimated by computing a volume the three coronal areas. Hemispheric Ischemic Damage comparisons were made using a non-paired Students T-test. * = $p < .001$.

The area of ischemic damage was significantly larger in the MCAO as compared to the sham-operated rats in the anterior and middle coronal sections, represented both as area of injury and area of injury as a percentage of the entire coronal section. The posterior coronal section showed a tendency toward a larger area of injury in MCAO animals relative to sham-operated controls. The area of the entire coronal section (infarcted and noninfarcted tissue) was 6.9% and 4.1% smaller in the anterior and posterior sections, respectively, in the MCAO versus sham operated animals. Although these decreases in coronal section area were small, they were statistically significant.

Combined middle cerebral and ipsiateral common carotid artery ligation caused ischemic cerebral tissue injury which was consistently greater in extent than that injury which occurs as a resut of sham operation alone. The area of injury was greatest in the anterior and middle coronal sections, which is consistent with the area of middle cerebral arterial distribution in the rat. The biological significance of the slightly smaller anterior and posterior coronal areas (infarcted and noninfarcted tissue) in MCAO animals remains unclear.

The Bioquant II image analysis system proved useful in quantitating ischemic injury as it was identified by Evans blue extravasation (blood brain barrier disruption). The variability in extent of ischemic cerebral tissue injury in this model is small enough that it can be reasonably anticipated that successful treatment can be detected by reduction in the lesion size.

The compounds of the present invention are determined to be active in this screen because their administration after arterial ligations leads to a reduction in the extent of cerebral tissue injury. Such reduction is shown in the comparisons of each compound to historical controls in each of the following Tables 3, 4, or 5. In each table n is the number of animals used. IP is intraperitoneal and $mm^2$ is area of damage expressed in square millimeters and $mm^3$ is hemispheric volume of damage expresses in cubic millimeters.

TABLE 3

| Diltiazem Historical Controls (n = 25) | |
| --- | --- |
| Infarct Areas ($\bar{x} \pm$ SE, $mm^2$) | Hemispheric Infarct Volume ($\bar{x} \pm$ SE, $mm^3$) |
| 10.85 ± 1.42 | 54.8 ± 4.62 |
| 15.40 ± 1.31 | |
| 13.10 ± 0.95 | |

| Effects of Diltiazem Administration (n = 5 per dose) | | | | |
| --- | --- | --- | --- | --- |
| mg/kg | (A) Anterior ($mm^2$) | (M) Medial $mm^2$ | (P) Posterior $mm^2$ | Infarct Volume $mm^3$ |
| 3 | 11.2 ± 2.1 | 9.75 ± 1.9 | 3.2 ± 2.5* | 32.4 ± 7.6* |
| 10 | 11.3 ± 1.4 | 8.3 ± 1.7* | 4.6 ± 2.6 | 32.0 ± 7.0* |
| 30 | 10.4 ± 1.6 | 11.7 ± 2.4 | 5.3 ± 2.8 | 37.9 ± 8.9 |

*Reduced relative to controls, $p < 0.05$
Diltiazem was given IP 30 minutes after the onset of cerebral ischemia and again 24 hours later. Forty-eight hours after arterial occlusions animals were sacrificed and estimates of infarct size were made using an image analysis system. Diltiazem treatment at 3, 10, and 30 mg/kg reduced the expected hemispheric cerebral infarct volume by 40, 41, and 30%, respectively.

TABLE 4

| Verapamil Historical Controls (n = 25) | |
| --- | --- |
| Infarct Areas ($\bar{x} \pm$ SE, $mm^2$) | Hemispheric Infarct Volume ($\bar{x} \pm$ SE, $mm^3$) |
| 10.85 ± 1.42 | 54.08 ± 4.62 |
| 15.40 ± 1.31 | |
| 13.10 ± 0.95 | |

| Effects of Verapamil Administration (n = 5 per dose) | | | | |
| --- | --- | --- | --- | --- |
| mg/kg | (A) Anterior ($mm^2$) | (M) Medial $mm^2$ | (P) Posterior $mm^2$ | Infarct Volume $mm^3$ |
| 3 | 11.6 ± 1.3 | 11.5 ± 1.7 | 5.9 ± 1.8 | 40.0 ± 6.2 |
| 10 | 13.1 ± 1.6 | 14.0 ± 1.3 | 12.8 ± 1.8 | 53.7 ± 5.7 |
| 30 | 8.3 ± 0.7* | 5.7 ± 1.1* | 3.0 ± 1.9 | 21.9 ± 4.6* |

*Reduced relative to controls, $p < 0.05$
Verapamil was given IP 30 minutes after the onset of cerebral ischemia and again 24 hours later. Forty-eight hours after arterial occlusions animals were sacrificed and estimates of infarct size were made using an image analysis system. Verapamil treatment at 30 mg/kg reduced the expected hemispheric cerebral infarct volume by 60%.

TABLE 5

| Nifedipine Historical Controls (n = 25) | |
| --- | --- |
| Infarct Areas ($\bar{x} \pm$ SE, $mm^2$) | Hemispheric Infarct Volume ($\bar{x} \pm$ SE, $mm^3$) |
| 10.85 ± 1.42 | 54.08 ± 4.62 |
| 15.40 ± 1.31 | |
| 13.10 ± 0.95 | |

| Effects of Nifedipine Administration (n = 5 per dose) | | | | |
| --- | --- | --- | --- | --- |
| mg/kg | (A) Anterior ($mm^2$) | (M) Medial $mm^2$ | (P) Posterior $mm^2$ | Infarct Volume $mm^3$ |
| 0.1 | 16.3 ± 2.0 | 15.0 ± 1.0 | 9.5 ± 2.5 | 55.2 ± 6.0 |
| 0.3 | 12.8 ± 0.9 | 13.0 ± 0.9 | 5.6 ± 1.1 | 43.9 ± 2.9 |
| 1.0 | 10.5 ± 0.8* | 9.1 ± 1.0* | 2.8 ± 1.5* | 30.2 ± 3.8* |

*Reduced relative to controls, $p < 0.05$
Nifedipine was given IP 30 minutes after the onset of cerebral ischemia and again 24 hours later. Forty-eight hours after arterial occlusions animals were sacrificed and estimates of infarct size were made using an image analysis system. Nifedipine treatment at 1.0 mg/kg reduced the expected hemispheric cerebral infarct volume by 44%.

In view of the observations that each of diltiazem, verapamil, and nifedipine decrease the area of damage after the onset of cerebral ischemia indicates the method of use of the present invention results in improved long term functional recovery after stroke in humans. Thus, the results of this study indicate a heretofore unknown advantage and beneficial effect for diltiazem, verapamil, and nifedipine in a model of stroke, as an effective agent in treating stroke.

I claim:

1. A method of use for treating stroke in a subject suffering therefrom comprising administering to said subject diltiazem, in an effective amount for treating stroke in a unit dosage form.

* * * * *